United States Patent [19]

Enustun et al.

[11] Patent Number: 5,172,977
[45] Date of Patent: Dec. 22, 1992

[54] ISOBARIC DILATOMETER

[75] Inventors: Bekir V. Enustun, Ames, Iowa; Turgut Demirel, Seattle, Wash.

[73] Assignee: Iowa State University Research Foundation, Inc., Ames, Iowa

[21] Appl. No.: 816,719

[22] Filed: Jan. 3, 1992

[51] Int. Cl.[5] .................... G01N 15/00; G01N 25/16
[52] U.S. Cl. ........................................... 374/55; 73/38
[58] Field of Search ................... 374/55, 54, 56, 45; 73/860, 38

[56] References Cited

U.S. PATENT DOCUMENTS

| | | |
|---|---|---|
| 3,085,441 | 4/1963 | Sarian . |
| 3,106,086 | 10/1963 | Hughel ................. 374/56 |
| 3,242,729 | 3/1966 | Keller . |
| 3,262,313 | 7/1966 | Hanna . |
| 3,327,524 | 6/1967 | Osgood ............... 374/54 X |
| 4,354,219 | 10/1982 | Akita . |
| 4,453,398 | 6/1984 | Demirel et al. . |
| 4,762,424 | 8/1988 | Baricevac et al. . |
| 4,923,307 | 5/1990 | Gilmore et al. . |

Primary Examiner—Daniel M. Yasich
Attorney, Agent, or Firm—Henderson & Sturm

[57] ABSTRACT

An isobaric mercury dilatometer for measurements of volume changes of solid specimens under a constant hydrostatic pressure either as a function of time or as a function of temperature. It includes structures for minimizing entrapment of air in the system, accurate computerized measurements in spite of the presence of some air. A two-piece stainless steel container is equipped with a horizontally situated volume-measuring stem, a filling device, an air vent and a temperature sensor. The specimen to be studied is placed in the container which is subsequently filled with mercury up to the stem. The volume changes of the specimen is reflected to the capacitance signals of an aluminum sleeve around the stem, while the temperature sensor generates temperature-related electronic signals. Both signals are received by a computer which translates them into volume and temperature data.

12 Claims, 1 Drawing Sheet 5,172,977

ISOBARIC DILATOMETER

TECHNICAL FIELD

This invention relates to a general purpose dilatometer and more particularly to one of a special design which permits measurement of volume changes of a solid specimen under a constant hydrostatic pressure, while the temperature of the specimen is measured simultaneously.

BACKGROUND ART

When the volume changes of a solid specimen are to be measured accurately by liquid displacement dilatometery, while filling the dilatometer, entrapment of a minute amount of air in the system is inevitable. In the case of a dilatometer of a conventional design, e.g., one with a vertical calibrated stem, the compressibility of this air creates a problem in making accurate measurements due to variation of hydrostatic pressure of the liquid in the dilatometer during its operation, especially if the dilatometer liquid is mercury. For instance, this problem is encountered in using such a dilatometer for measurements of expansive properties of concrete and other construction materials.

DISCLOSURE OF THE INVENTION

The present invention includes a dilatometer made of stainless steel and glass, equipped with a calibrated capillary stem situated in a horizontal plane, instead of extending vertically as in conventional forms, to keep the hydrostatic pressure in the system constant during the volume measurements, irrespective of location of the liquid meniscus in the stem. The invention also contains provisions for minimizing air entrapment and for electronic measurements of volume changes and of internal temperature simultaneously.

An object of this invention is to provide a dilatometer which allows volume change measurements of solid specimens under a constant hydrostatic pressure of the liquid.

However, even constant hydrostatic pressure may not solve the problem if a substantial amount of air is present in the dilatometer, because of variations in the barometric pressure and occasional mechanical vibrations during measurements. Therefore, a further object of this invention is to provide a dilatometer container of a special geometry which minimizes air entrapment.

Another object of this invention is to provide a dilatometer equipped with a liquid filling attachment which also minimizes introduction of air during filling.

A further object of this invention is to provide a dilatometer which allows measurements of the temperature of the specimen concurrently with volume measurements.

A still further object of this invention is to provide an easy-to-construct, durable and easy-to-operate dilatometer suitable for computerized measurements.

Other objects, advantages, and novel features of the present invention will become apparent from the following detailed description of the invention when considered in conjunction with the accompanying drawings.

BEST MODE FOR CARRYING OUT THE INVENTION

Figure 1:
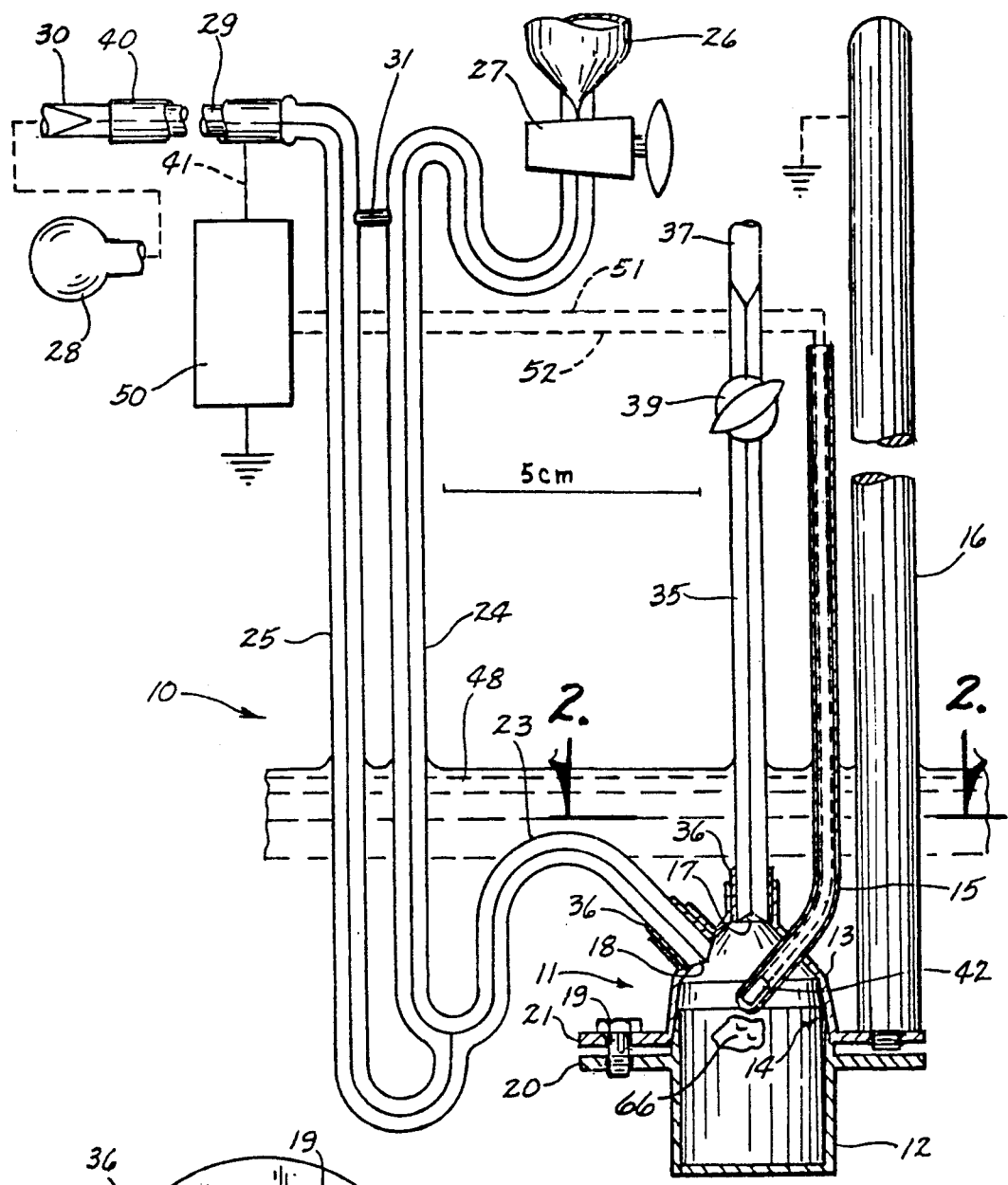
FIG. 1 is a front view of a preferred embodiment of the invention showing a sectional view of its container, and also showing schematically the electronic circuits associated therewith.
Figure 2:
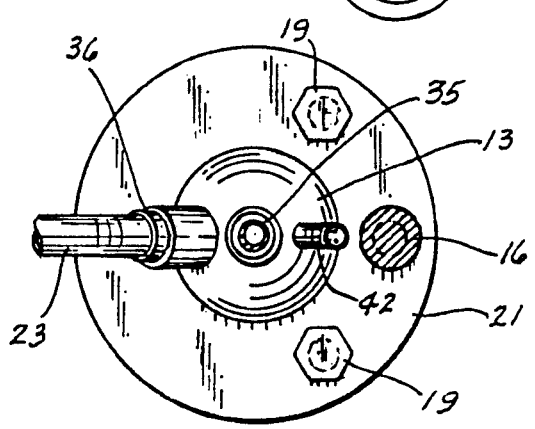
FIG. 2 is a top view taken along line 2—2 of FIG. 1.

Referring now to the drawings wherein like reference numerals designate identical or corresponding parts on both figures, FIG. 1 shows an isobaric mercury dilatometer (10) constructed in accordance with the present invention, having a stainless steel container (11) of about 30 ml capacity consisting of a cylindrical and flanged cup (12) and a conical and flanged cover (13) fitting together by a precision-machined conical joint (14). The cover (13) carries a tubular stainless steel housing (15) for insertion of a temperature sensor, and a 40 cm long vertical stainless steel handle bar (16). The cover (13) is also equipped with a top outlet (17) and a slanting outlet (18). The container is assembled by fastening the cup (12) to the cover (13) by three equally spaced screws (19) through respective flanges (20) on cup (12) and (21) on cover (13).

A first glass tube (23) leads from cover (13) to a mercury filling tube (24) and a volume measuring tube (25). A mercury holding reservoir (26) of about 10 ml capacity is connected to tube (24) and a capillary stopcock (27) is disposed in the 1 mm bore of capillary tubing (24). A horizontally situated and calibrated capillary stem (29) widens at the end (30). A reinforcement rod (31) connects tubes (24) and (25). The stem (29) can be made of a glass micro-pipette of about 0.15 ml capacity. A bulb (28) of rubber or the like is disposed over the end of stem (29), when needed, for reasons which will be explained below.

A second glass attachment (35) functions as an air vent during filling and as an outlet for discharging mercury at the end of a run. Glass tube (35) consists of a 1 mm bore vertical capillary tubing widened at the vent or top (37), and having a capillary stopcock (39).

The glass tubes (23) and (35) are permanently connected to outlets (18) and (17) respectively of the cover (13), by glass-to-metal seals (36), and firmly and securely fastened to the handle (16) by a horizontal bar and cuffs (not shown).

The invention operates in conjunction with an electronic volume measuring device consisting of an aluminum sleeve (40) about 22 cm long slipped over the calibrated stem (29) and connected to the circuitry of a microcomputer (50) by a lead (41). This part of the operation is like U.S. Pat. No. 4,453,398 to Demirel et al. An electronic temperature sensor (42) such as a thermistor, thermocouple, platinum resistance, or the like is inserted into its housing on cover (13) as shown in FIG. 1, and is connected to the circuitry of the same computer (50) by leads (51) and (52).

In operation, the sample is placed in the dilatometer cup (12) either before or after partly filling the cup with mercury, depending on the type of the sample. The cup (12) is attached to the dilatometer cover (13) tightly by means of the three screws (19) mentioned above. When the stopcock (27) is closed and the stopcock (39) is in an open position, the reservoir (26) is filled with mercury. By gradually opening the stopcock (27), additional mercury is introduced into the dilatometer until all air is expelled from it through the top (37) and the mercury rises in the capillary tubing (35) past and above the stopcock (39). The stopcocks (27) and (39) are then closed.

The dilatometer (10) is then immersed in a temperature controlled bath (48) as shown in FIG. 1. After thermal equilibration, by opening the stopcock (27) again, a small amount of additional mercury is introduced until the mercury meniscus in the left hand side limb (25) of the capillary tubing rises and enters the calibrated stem (29). The mercury meniscus is positioned accurately in the stem (29) as desired by opening the stopcock (27) momentarily and applying a small opposing pressure to the open end of the calibrated stem (29) by means of rubber bulb (28).

Then the aluminum sleeve (40) is slipped over the stem (29) and the collection of data on the change of volume of the system may start either at a constant temperature as a function of time, or while the temperature of bath (48) changes according to a preset program, as a function of temperature. In either case, an electronic signal generated by the aluminum sleeve (40), which is proportional to the capacitance across the aluminum sleeve (40) and the mercury thread in the stem (29), and therefore is a linear function of the volume of mercury in the stem, is fed to the microcomputer (50). If the temperature data is also to be recorded, temperature-related similar signals generated by the temperature sensor (42) are supplied to the same computer (50) by leads (51) and (52). The computer (50) saves both types of signals and converts them either to a set of volume versus time data, or to a set of volume versus temperature data, depending on the nature of the study.

In the latter case, the measured volume changes of the system consisting of mercury, container and the specimen can be processed further to resolve the volume changes of the specimen alone, by the methods well known to the experts of the state of the art.

Accordingly, it will be appreciated that the preferred embodiment shown and described does indeed accomplish the aforementioned objects. Obviously, many modifications and variations of the present invention are possible in light of the above teachings. It is therefore to be understood that, within the scope of the appended claims, the invention may be practiced otherwise than as specifically described.

We claim:

1. A dilatometer apparatus for measuring volume changes of solid specimens comprising:
   means for sealingly holding a solid specimen having a volume change to be measured, said holding means including a container;
   means connected to said container for filling said container with an electrically conductive liquid; and
   means for measuring changes in volume of said solid specimen comprising:
   (a) conduit means operatively fluidly connected at one end thereof to said holding means for permitting said conductive liquid to flow therethrough due to changes in volume of said solid specimen;
   (b) an electrically conductive sleeve disposed about a longitudinal axis;
   (c) a stem portion of said conduit means being surrounded by said conductive sleeve, the longitudinal axis of said conductive sleeve and stem portion of said conduit means within said conductive sleeve is horizontally disposed, said stem portion of said conduit means being remote from said container; and
   (d) means associated with said conductive sleeve for generating an electronic volume signal which is proportional to a capacitance across the conductive sleeve and that part of the conductive liquid in the stem portion of the conduit means which is surrounded by said conductive sleeve, said capacitance being a linear function of the volume of conductive liquid in the stem portion.

2. The apparatus of claim 1 including:
   a computer;
   means for inputing said electronic volume signal to said computer; and
   program means associated with said computer for plotting the change in volume of said solid specimen with respect to time.

3. The apparatus of claim 1 wherein said conductive liquid is mercury.

4. The apparatus of claim 1 wherein said conductive sleeve is constructed of aluminum.

5. The apparatus of claim 1 including bath means for surrounding said holding means with a liquid.

6. The apparatus of claim 5 including means for changing the temperature of said liquid within said bath means and thereby measuring the temperature of said solid specimen.

7. The apparatus of claim 6 including means for measuring the temperature of said conductive liquid in said container and producing and electronic temperature signal corresponding thereto.

8. The apparatus of claim 7 including:
   a computer;
   means for inputing said electronic volume signal, which is a linear function of the volume of the conductive liquid in said stem portion to said computer; and
   means for inputing said electronic temperature signal to said computer.

9. The apparatus of claim 7 including:
   a computer;
   means for inputing said electronic volume signal to said computer;
   means for inputing said electronic temperature signal to said computer; and
   program means associated with said computer for plotting the change in volume of said solid specimen with respect to the changes of temperature of solid specimen.

10. A dilatometer apparatus for measuring volume changes of solid specimens comprising:
    means for sealingly holding a solid specimen having a volume change to be measured, said holding means including a container;
    means connected to said container for filling said container with an electrically conductive liquid, said filling means comprising:
    a) a supply reservoir for supplying conductive liquid to said container;
    b) supply means operatively fluidly connecting said supply reservoir to said container;
    c) supply valve means operatively disposed in said supply line means for selectively permitting conductive liquid to flow to said container;
    d) air purging line means fluidly connected to said container; and
    e) air purging valve means operatively disposed within said air purging line means for selectively either letting air escape from said air purging line means or preventing conductive liquid from escaping from said air purging line means; and means for measuring changes in volume of said solid specimen comprising:

(a) conduit means operatively fluidly connected at one end thereof to said holding means for permitting said conductive liquid to flow therethrough due to changes in volume of said solid specimen;

(b) an electrically conductive sleeve disposed about a longitudinal axis;

(c) a stem portion of said conduit means being surrounded by said conductive sleeve; and (d) means associated with said conductive sleeve for generating an electronic volume signal which is proportional to the capacitance across the conductive sleeve and that part of the conductive liquid in the stem portion of the conduit means which is surrounded by said conductive sleeve, said capacitance being a linear function of the volume of conductive liquid in the stem portion.

11. The apparatus of claim 10 wherein said conduit means is operatively fluidly connected to said supply line means whereby said supply reservoir can supply conductive liquid to both said container and to said conduit means when said supply valve means is opened.

12. The apparatus of claim 10 wherein said other end of said conduit means, adjacent to said stem portion thereof, includes means for applying pressure against conductive liquid disposed in said stem portion whereby the position of the end of said conductive liquid in said stem portion can be regulated in conjunction with the opening of said supply valve means.

* * * * *